(12) United States Patent
Catalano et al.

(10) Patent No.: US 11,413,134 B1
(45) Date of Patent: Aug. 16, 2022

(54) NIPPLE IMPLANT SYSTEM

(71) Applicants: Eric J. Catalano, Hecker, IL (US); Maddie A. Singer, Memphis, TN (US)

(72) Inventors: Eric J. Catalano, Hecker, IL (US); Maddie A. Singer, Memphis, TN (US)

(73) Assignee: Nipple Implant System, LLC, Heckler, IL (US)

( * ) Notice: Subject to any disclaimer, the term of this patent is extended or adjusted under 35 U.S.C. 154(b) by 812 days.

(21) Appl. No.: 15/893,224

(22) Filed: Feb. 9, 2018

Related U.S. Application Data

(63) Continuation-in-part of application No. 15/278,476, filed on Sep. 28, 2016, now abandoned.

(51) Int. Cl.
*A61F 2/12* (2006.01)
*A61F 2/52* (2006.01)
*A61F 2/50* (2006.01)

(52) U.S. Cl.
CPC .................. *A61F 2/12* (2013.01); *A61F 2/52* (2013.01); *A61F 2002/5001* (2013.01); *A61F 2002/526* (2013.01)

(58) Field of Classification Search
CPC ...... A61F 2/12; A61F 2/52; A61F 2220/0041; A61F 2002/256; A61F 2002/5001; A61F 2210/0014; A61F 2230/0067; A61F 2230/0091; A61F 2230/0093
See application file for complete search history.

(56) References Cited

U.S. PATENT DOCUMENTS

| | | | |
|---|---|---|---|
| 4,241,737 A | 12/1980 | Schmidt | |
| 4,778,465 A | 10/1988 | Wilkins | |
| 5,171,321 A | 12/1992 | Davis | |
| 6,136,028 A * | 10/2000 | Weber-Unger | A61F 2/52 623/7 |
| 2004/0010311 A1 | 1/2004 | Reynolds | |
| 2014/0336759 A1 | 11/2014 | Martin | |

* cited by examiner

*Primary Examiner* — Jerrah Edwards
*Assistant Examiner* — Rokhaya Diop
(74) *Attorney, Agent, or Firm* — Grace J. Fishel

(57) ABSTRACT

A nipple implant system wherein a nipple prosthetic device is attached to a microdermal anchor without the need for invasive surgery. The microdermal anchor is inserted through a hole punched at a selected locus. The nipple prosthetic device is configured for attachment to the microdermal anchor. An areola may be tattooed around the locus or the nipple prosthetic device may include a skirt simulating an areola to make the construction complete.

12 Claims, 8 Drawing Sheets

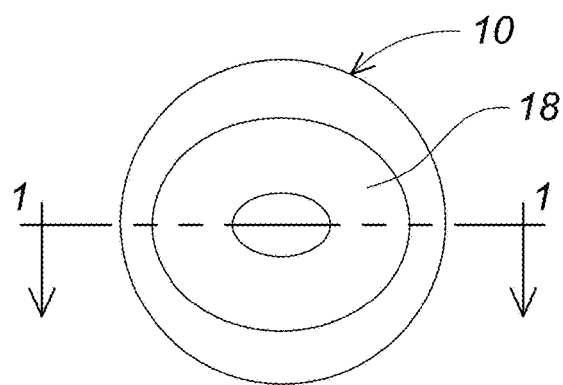
Fig. 3
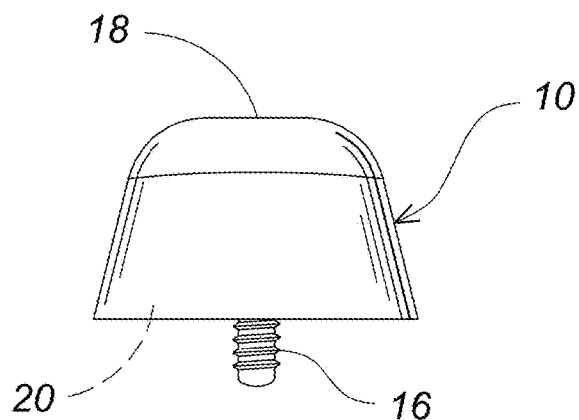
Fig. 2
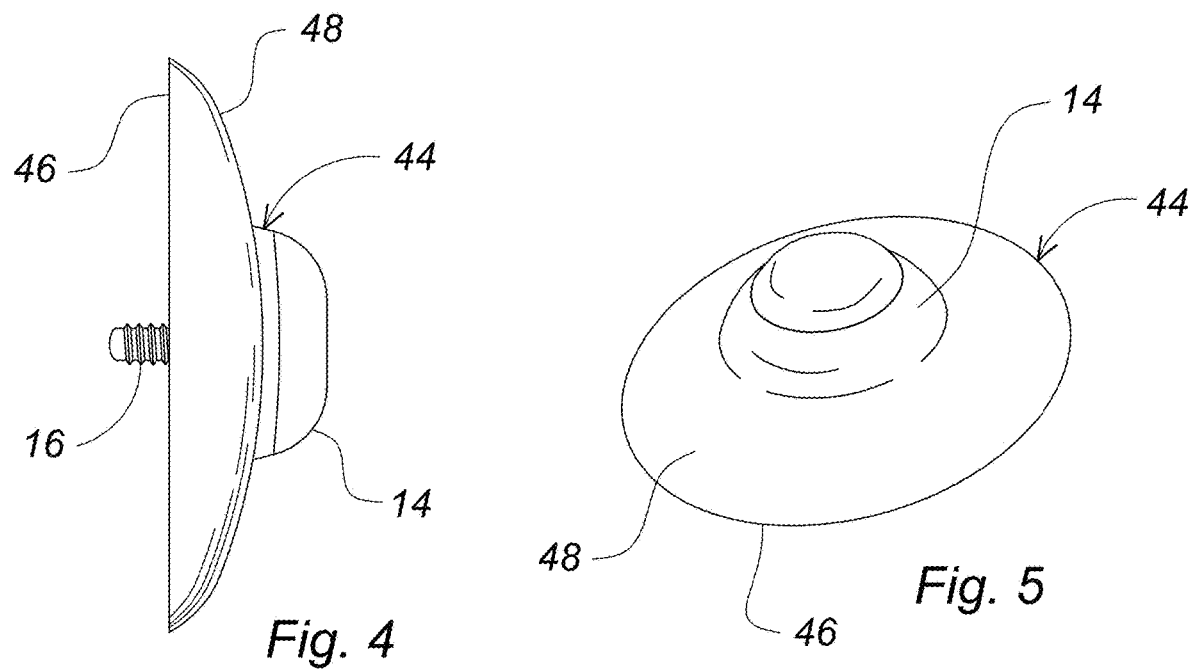
Fig. 4
Fig. 5

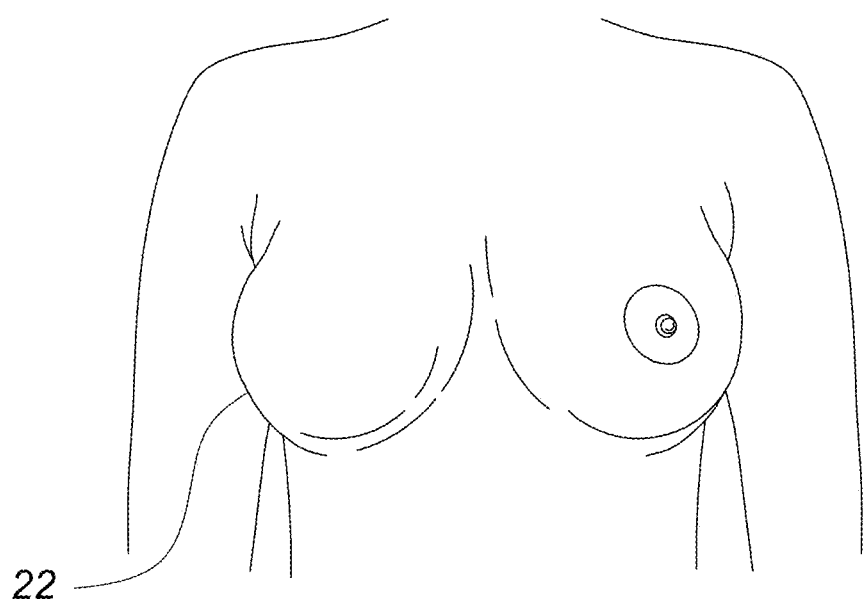
*Fig. 9*
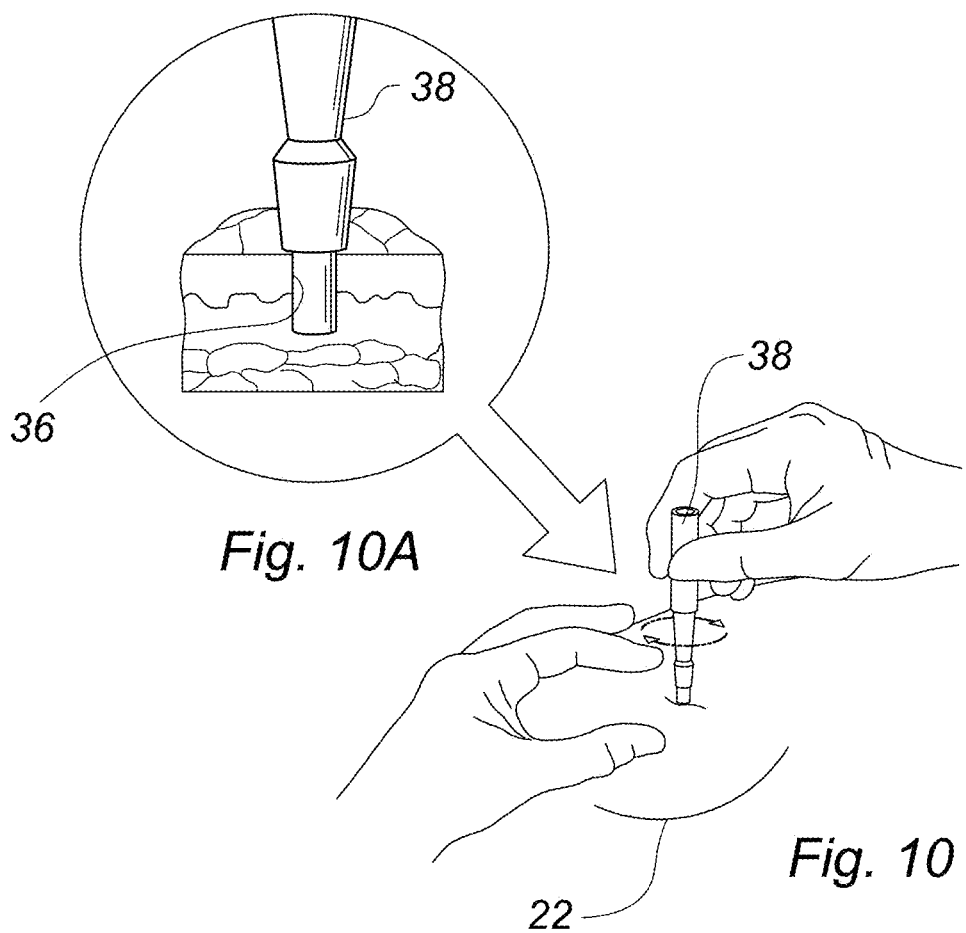
*Fig. 10A*
*Fig. 10*

NIPPLE IMPLANT SYSTEM

BACKGROUND OF THE INVENTION

Field of the Invention

The present invention relates to a nipple implant system including an artificial nipple prosthetic device attachable with a microdermal anchor to a human breast.

Brief Description of the Prior Art

After a mastectomy, either because a patient was diagnosed with breast cancer or was at very high risk of developing it in the future, it is possible for a surgeon to rebuild the breast or breasts such that the reconstruction simulates the size and shape of the member that was removed. While breast reconstruction rebuilds the shape of the breast, it does not restore the areola or the nipple and a reconstructed breast without an areola and nipple looks like a face without features. While the areola and to some extent a nipple may be simulated by tattooing, currently additional surgery is required to reconstruct a protruding nipple. For this a flap of skin is harvested from another part of the body and surgically attached. The surgery is invasive with a long recovery time, expensive and not likely to be covered by medical insurance. In addition, a surgically reconstructed nipple typically loses some projection over time during the normal healing process. There have also been surgically implantable areola and nipple prosthetics such as describes in U.S. Pat. No. 4,778,465 and US 2014/0336759 for which the wearer must undergo expensive and sometimes dangerous surgical procedures to have removed in the event of a defect.

Hence there is a vital need for a prosthetic nipple and areola that may be applied without the need for invasive surgery, which is inexpensive to manufacture and which may be offered in a variety of sizes, shapes and colors.

BRIEF SUMMARY OF THE INVENTION

In view of the above, it is an object of the present invention to provide a nipple implant system that does not require for invasive surgery. It is also an object to provide a prosthetic nipple that is inexpensive to manufacture and may be provided in different sizes, shapes and colors. Other objects and features of the invention will be in part apparent and in part pointed out hereinafter.

In accordance with the invention, a first nipple implant system includes a nipple prosthetic device and a microdermal anchor. In an embodiment the nipple prosthetic device includes a nipple portion and a post. The nipple portion is formed of an alloplastic material and has a substantially rounded apex portion and a substantially concave base. The post has a head embedded in the base of the nipple portion and is formed of a rigid material with threads adapted for threaded engagement with the microdermal anchor. An areola may be attached to the nipple portion or tattooed around the nipple to make a breast reconstruction complete.

In a second preferred embodiment of the invention, a nipple and areola are formed of an alloplastic material with the nipple portion configured for magnetic attachment to a magnet supported by a microdermal anchor and with an underside of the areola portion supported with an acrylic plastic. A skin lotion may be applied to the acrylic plastic to stabilize the magnetic connection and prevent accidental release of the prosthetic from a user's chest.

Both embodiments of the prosthetic device may be installed by a skilled operator with or without medical supervision.

The invention summarized above comprises the constructions and methods hereinafter described, the scope of the invention being indicated by the subjoined claims.

BRIEF DESCRIPTION OF THE SEVERAL VIEWS OF THE DRAWING

In the accompanying drawings, corresponding reference characters refer to corresponding parts throughout the several views of the drawings in which:

FIG. 2 is a side elevation of the prosthetic nipple device;

FIG. 3 is a top plan view of the prosthetic nipple device;

FIG. 4 is a side elevation of a second prosthetic nipple device with a skirt simulating an areola;

FIG. 5 is a top perspective of the second prosthetic nipple device;

FIG. 9 illustrates a patient with one breast having undergone post mastectomy reconstruction;

FIG. 10 illustrates a punch making a hole in the skin at the locus where a microdermal anchor is to be installed on the patient's reconstructed breast;

FIG. 10A is a detail from FIG. 10 on an enlarged scale;

DETAILED DESCRIPTION OF THE INVENTION

Figure 1:
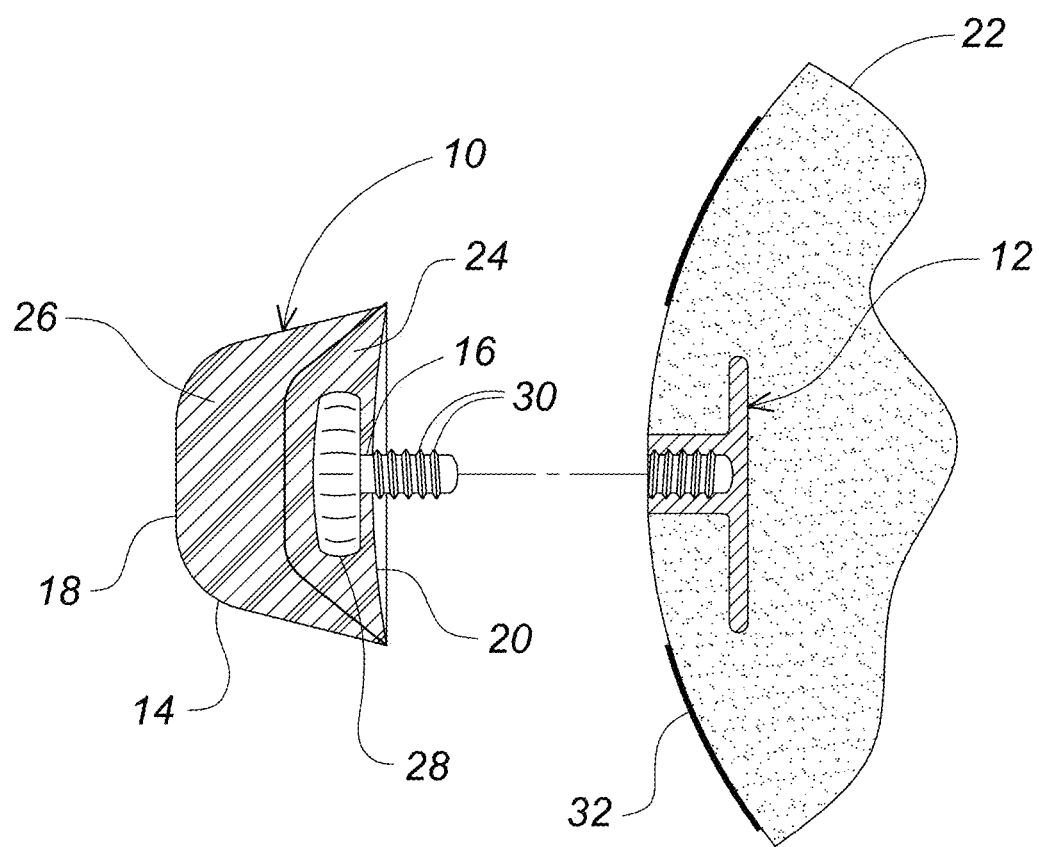
FIG. 1 is an x-ray exploded view of a nipple implant system including a first prosthetic nipple device for attachment to a microdermal anchor in accordance with the present invention.
Figure 8:
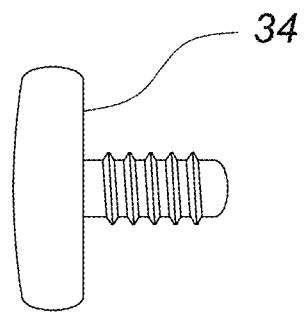
FIG. 8 is a side elevation of a healing nub for attachment to the microdermal anchor.

The following detailed description is merely exemplary in nature and is not intended to limit the described embodiments or the application and uses of the described embodiments. Hence, specific dimensions and other physical characteristics relating to the embodiments disclosed herein are not to be considered as limiting, unless the claims expressly state otherwise.

Referring to the drawings more particularly by reference character, reference number 10 refers to an artificial nipple prosthetic device in accordance with the present invention. Device 10 is adapted for attachment to a microdermal anchor 12 as shown in FIG. 1.

As shown in FIGS. 1-3, device 10 includes a nipple 14 mounted on a post 16. Nipple 14 is formed of an alloplastic material such as a silicone elastomer and has a substantially rounded apex 18 and a concave base 20 to conform to the shape of a human breast 22 and to cup over anchor 12. As shown in FIG. 1, a lower portion 24 of the nipple may be formed of a stiffer material that an upper portion 26. Post 16 has a head 28 embedded in lower portion 24 of nipple 14 and is formed of a rigid material including metals and hard plastics. Head 28 may be knurled or otherwise textured such that it does not twist out of lower portion 24. When post 16 is formed for steel or titanium, it may be preferred that the material be the same material as is used for anchor 12. Post 16 is threaded 30 for attachment to microdermal anchor 12. For example, the outside diameter of the threads 30 may be about 1.2 mm or 1.6 mm, those being inside diameters of commercially available microdermal anchors 12. It will be understood that post 16 may have other outside diameters as required to match the threads of the particular microdermal anchor 12.

As a general rule, nipple 14 has a diameter of about ½ inch and a height of about ½ inch but the nipple may be offered in other diameters and heights depending on the nipple shape desired. In addition, the material out of which nipple 14 is formed may be colored such that it looks like a natural nipple on the breast being reconstructed.

In use, device 10 is attachable to a human breast most usually a breast that has undergone breast reconstruction as shown in FIG. 9 but the use of the device is not limited thereto. When used as a final component of breast reconstruction, an areola 32 may be tattooed in the region where the patient desires device 10 to be installed. Different colored inks and different sized needles may be used to give the tattoo shading and depth so that areola 32 looks realistic. Ideally areola 32 is tattooed about a week or so before device 10 is installed but device 10 may be installed concurrently or tattooing may be done after the device is installed.

Figure 6:
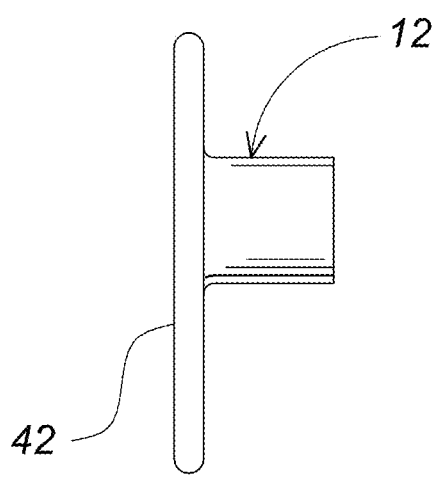
FIG. 6 is a side elevation of a microdermal anchor.
Figure 7:
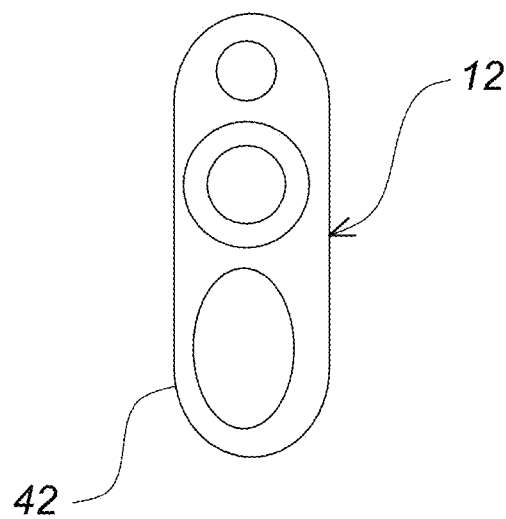
FIG. 7 is a top view of the microdermal anchor.
Figure 11:
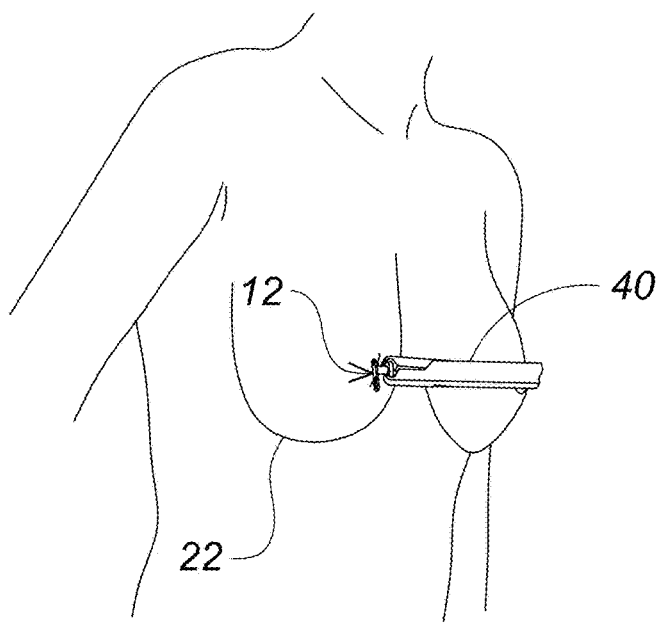
FIG. 11 shows a pair of hemostats gripping a nub of the microdermal anchor for inserting the anchor in the hole made by the punch.

As a first step to attaching device 10, a microdermal anchor 12 is selected. A representative but non-limiting microdermal anchor 12 is shown in FIGS. 6-7. Some microdermal anchors 12 include a base plate with no holes, one hole or two holes. Those with no holes are easier to remove, if necessary, but those with holes have the advantage that the tissue may grow though the base plate, forming a more secure placement. For use in the installation of device 10, microdermal anchor 12 includes a healing nub 34 which is screwed into the anchor.

Figure 12:
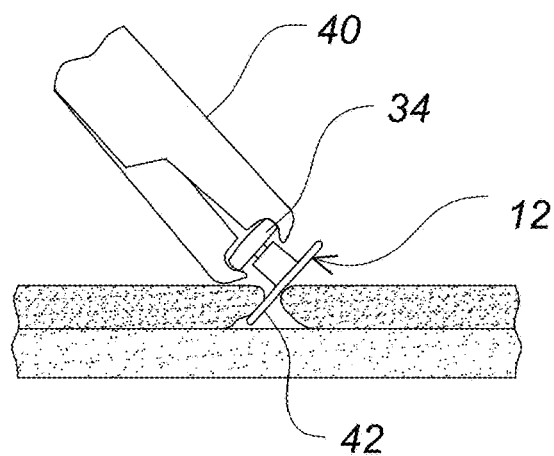
FIG. 12 shows the hemostats inserting a long leg of the microdermal anchor into the hole.
Figure 13:
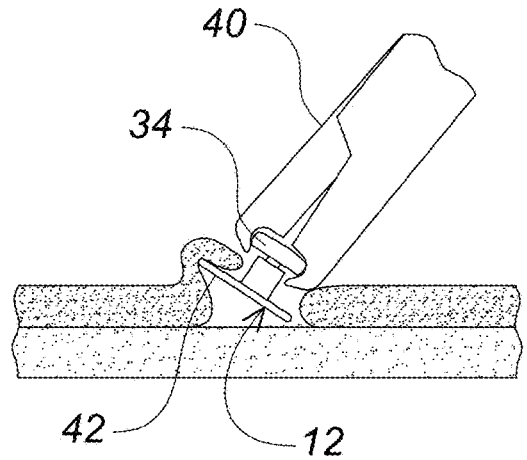
FIG. 13 shows the hemostats leaning the microdermal anchor back and placing the short leg in place.

In use, an operator will scrub and then mark the locus where the patient wants device 10 to be installed. As shown in FIGS. 10 and 10A, a hole 36 is then made on the mark with a needle or punch 38. Once hole 36 is formed, the operator may hold healing nub 34 of microdermal anchor 12 with a pair of forceps or hemostat 40 and use a longer leg 42 of microdermal anchor 12 to elevate the skin as shown in FIG. 12. Forceps or hemostat 40 is then used to lean microdermal anchor 12 as shown in FIG. 13 to place the shorter leg of anchor into place thereby completing the installation of the microdermal anchor. The installation of microdermal anchor 12 is not highly painful and does not usually require the use of anesthetics. Preferably microdermal anchor 12 should be allowed to heal in place for several weeks.

Figure 14:
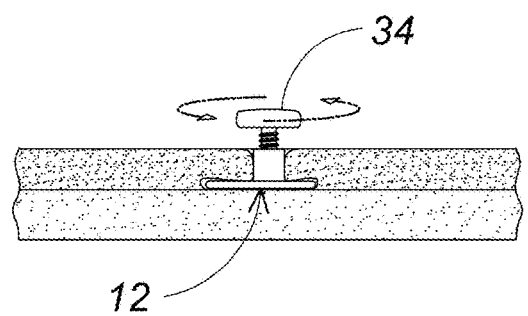
FIG. 14 shows the healing nub being unthreaded from the microdermal anchor preparatory to attachment of a prosthetic nipple device.

With microdermal anchor 12 in place, healing nub 34 is unthreaded as shown in FIG. 14 from microdermal anchor 12 and replaced with device 10 as shown in FIG. 1. Upon attachment to microdermal anchor 12, nipple 14 projects outwardly from the breast is a realistic manner. With proper selection of the size, shape and color of nipple 14, device 10 looks very realistic, similar to what the patient's nipple looked like before breast surgery thereby making breast reconstruction complete.

The above described installation of device 10 and formation of areola 32 may be done in a piercing and tattooing salon. While the procedure requires a highly skilled operator, the services of a doctor are not required. However for those patients who prefer, the procedure may provided in a clinical environment under the auspices of a plastic surgeon or the like.

Figure 15:
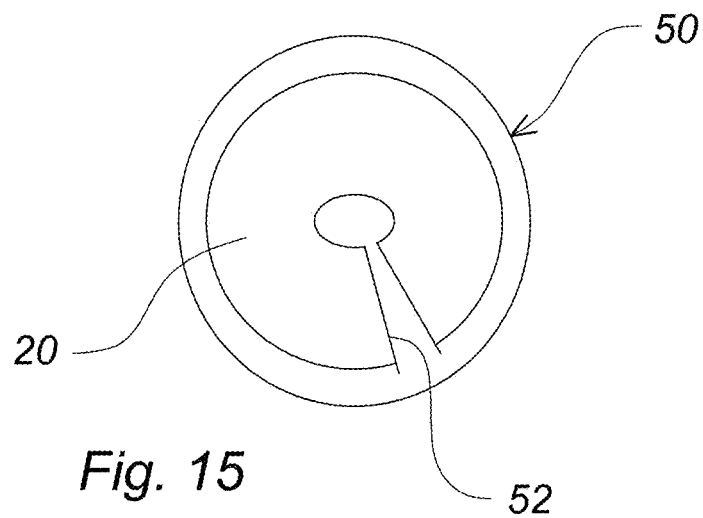
FIG. 15 is a bottom plan view of a third prosthetic nipple device.
Figure 16:
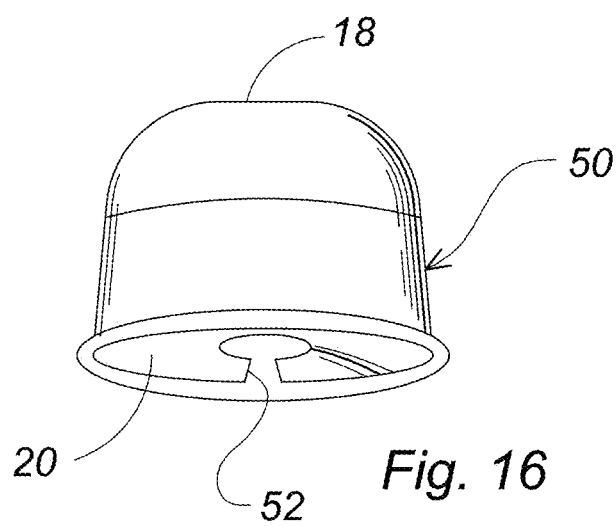
FIG. 16 is a bottom perspective view of the third prosthetic nipple device.
Figure 17:
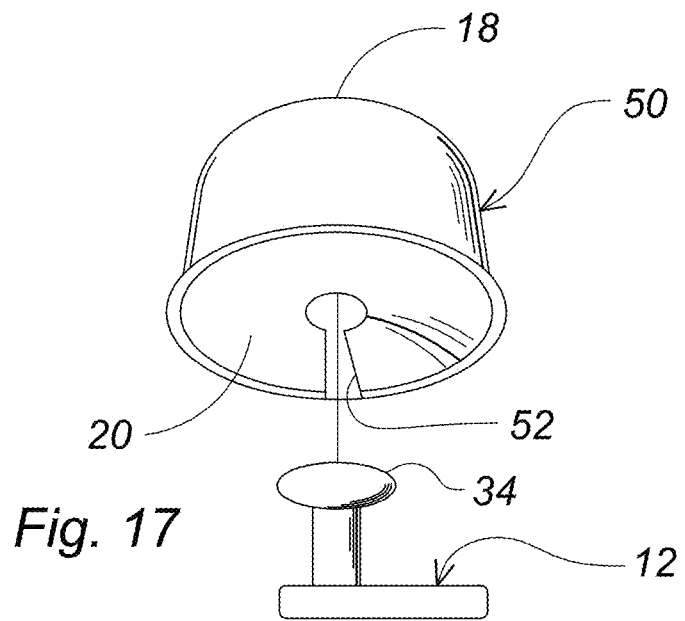
FIG. 17 is an exploded view of the third prosthetic nipple device in process of being snapped onto the healing nub of a microdermal anchor.

A second nipple prosthetic device 44 is shown in FIGS. 4 and 5. It is substantially like the device shown in FIGS. 1-3 except that a skirt 46 is attached to lower portion 24. Skirt 46 has a slightly raised area 48 surrounding nipple 14 to give a very natural appearance of an areola. Skirt 46 like nipple 14 may be appropriately colored. A third nipple prosthetic device 50 is shown in FIGS. 15-17. In this embodiment, lower portion 24 of nipple 14 includes a slit 52 which may be used to frictionally engage healing nub 34 which is left in place in microdermal anchor 12.

Figure 18:
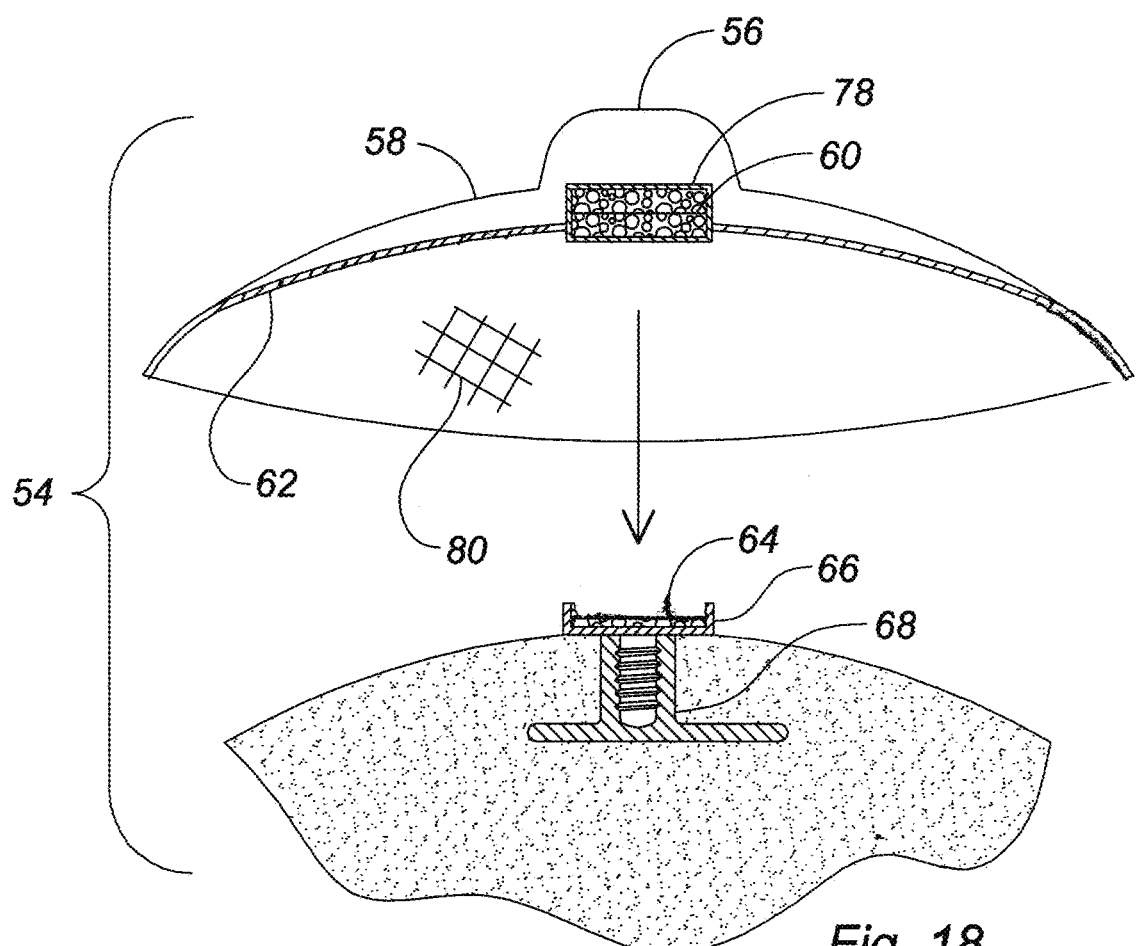
FIG. 18 is an exploded view of a fourth prosthetic device in process of being magnetically attached to a microdermal anchor.
Figure 19:
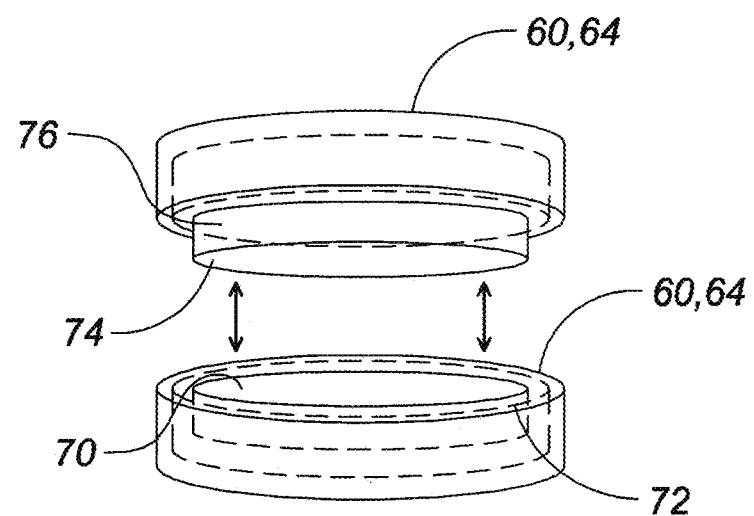
FIG. 19 illustrates a side view of magnets on the prosthetic device and on the microdermal anchor with mating male and female portions; and, FIG. 20 is a photograph of the prosthetic device removed from a mold before flashing around the areola is removed.

Turning to FIGS. 18 and 19, a fourth and preferred prosthetic device 54 includes a nipple 56 and an attached areola 58 formed of silicone preferably platinum cure silicone. Embedded in an underside of nipple 56 is a rare earth magnet 60 such as a neodymium magnet. For increased magnetic flux, magnets 60 may be stacked as shown. A ring 62 formed of a hard acrylic material surrounds an exposed face of magnet 60 and is attached to an underside of areola 58 to provide support just short of the periphery (e.g., ⅛ inch). Suitable hard acrylics include thermoplastic materials such as biocryl.

A magnet or ferromagnetic plate 64 is attached to a nub 66 threaded into a microdermal anchor 68 in the manner of healing hub 34 discussed above. Magnet 64 like magnet 60 is preferably a rare earth magnet and positioned on nub 66 such that the magnetic portions of magnets 60, 64 are opposed to each other. Nub 66 may be formed of ASTM F-136 titanium or the like. It will be further understood that either of magnets 60, 64, preferably magnet 64, may be replaced with a ferromagnetic plate to the same end. To stabilize the magnetic connection one of the magnets 60, 64 has a depressed female portion 70 and a raised rim 72 forming the mating male portion and the other magnet has a raised male portion 74 and a depressed rim 76 section forming the mating female portion. The mating sections guide and seat the magnetic portions together for securely adjoining the prosthetic device 54 to the microdermal anchor 68. As shown in FIG. 18, nub 66 has a rim within which magnetic or ferromagnetic plate 64 is recessed and magnet 60 slips into the recess wherein it is magnetically seated. The mated magnets 60, 64 prevent accidental release of prosthetic device 54 during wear, while being operative to readily disconnect when subjected to pulling force, mitigating injury to a user. In one embodiment a layer of a thermoplastic 78 such as used in mouth guards surround magnet 60 for the purpose of forming a solid bond with the silicone forming the nipple and areola as described below.

Figure 20:
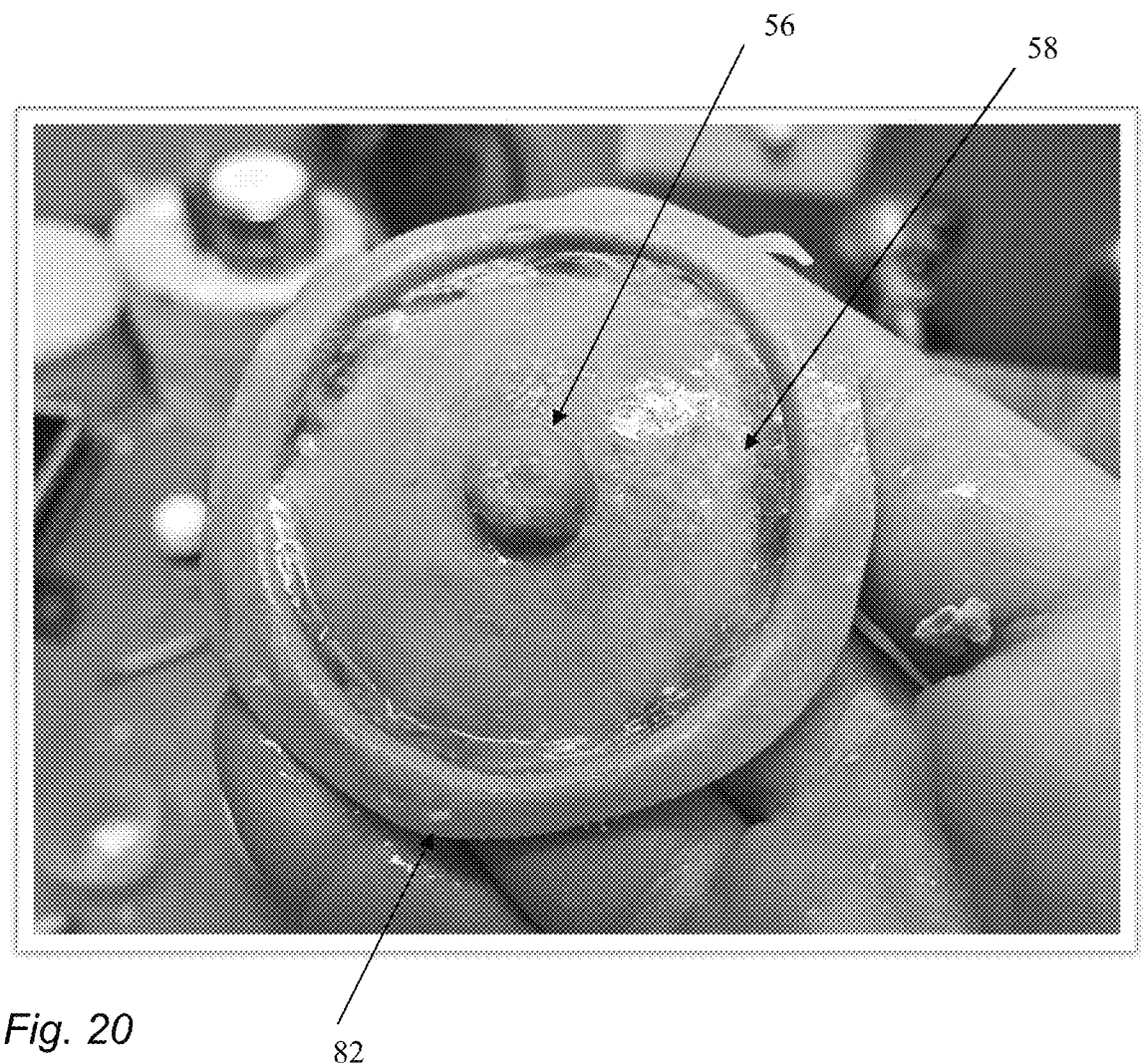

Prosthetic device 54 may be formed as follows: Plastic clad magnet 60 is cleaned with acetone or the like and a primer is applied. Magnet 60 is slipped into a mold cavity surrounded by acrylic ring 62 which is cleaned and treated with a primer. Colors and fibers may be mixed into a batch of silicone to simulate the color and texture of nipple 56 and areola 58 which may be particularized to the user. The prepared mold is then filled with the silicone mixture and oven cured. After curing the part is removed from the mold and any flashing 82 (FIG. 20) trimmed from areola 58. Magnet 64 is attached to nub 66, microdermal anchor 68 installed and nub 66 threaded into anchor 68.

In use, anchor 68 is installed as described above and fourth prosthetic device 54 prepared for attachment to magnet 64. A layer of a body lubricant such as petroleum jelly 80 is applied to ring 62 and the unsupported periphery of areola 58. The petroleum jelly vacuum attaches the prosthetic device 54 to the skin such that it does not become accidentally removed as for example when a user removes inner clothing. While petroleum jelly has been found satisfactory skin adhesives may also be used if a stronger or more permanent attachment is desired.

Although several embodiments are specifically illustrated and described herein, it will be appreciated that many modifications and variations of the present invention are possible in light of the above teachings and within the purview of the appended claims without departing from the spirit and intended scope of the invention.

What is claimed:

1. A nipple implant system comprising a microdermal anchor and a nipple prosthetic device, said microdermal anchor having a flat base plate and a threaded stem, said flat base plate adapted to be embedded in the skin of a user with said threaded stem adapted to extend through a pierced hole in the user's skin,
    said nipple prosthetic device formed of silicone with a substantially rounded apex portion and a substantially concave base, said concave base having means for attachment of the nipple prosthetic device to the stem of the microdermal anchor.

2. The nipple implant system of claim 1 wherein the apex portion of the nipple prosthetic device is formed of a softer material than the concave base of the nipple prosthetic device.

3. The nipple implant system of claim 2 wherein the means for attachment of the nipple prosthetic device to the microdermal anchor comprises a post formed of a rigid material embedded in the lower portion of the nipple prosthetic device with threads adapted for engagement with the stem of the microdermal anchor.

4. The nipple implant system of claim 2 wherein a dermal implant nub is attached to the stem of the microdermal anchor and wherein the means for attachment of the nipple prosthetic device to the microdermal anchor comprises a slit in the lower portion of the nipple prosthetic device for frictional engagement of the dermal implant nub.

5. The nipple implant system of claim 1 wherein the nipple prosthetic device has a skirt simulating an areola attached to the base.

6. The nipple implant system of claim 5 wherein the silicone in the nipple prosthetic device and skirt are colored to match a selected skin color.

7. The nipple implant system of claim 1 wherein the silicone is platinum cure silicone.

8. The nipple implant system of claim 1 having a first magnetic or ferromagnetic member on the nipple prosthetic device and a second magnetic or ferromagnetic member on the microdermal anchor, said first magnetic or ferromagnetic member having a male mating portion and said second magnetic or ferromagnetic member having a female mating portion.

9. A nipple implant system comprising a microdermal anchor and a nipple prosthetic device, said nipple prosthetic device formed of silicone with a substantially rounded apex portion and a base with an attached skirt simulating an areola, a first magnetic or ferromagnetic member received in a recess in the base with an acrylic ring attached to an underside of the skirt for support and with an aperture in the base in registry with the first magnetic or ferromagnetic member through which the magnetic or ferromagnetic member extends,
    said microdermal anchor having a nub threaded into the microdermal anchor, said nub having a second magnetic or ferromagnetic member attached to the nub for magnetic attachment of the nipple prosthetic device through the first magnetic or ferromagnetic member attached to the nipple prosthetic device.

10. The nipple implant system of claim 9 wherein one of said first magnetic or ferromagnetic member on the nipple prosthetic device and the second magnetic or ferromagnetic member on the microdermal implant has a first female cavity section and a first raised male rim and second of said members has a second raised male rim and a second female cavity section, wherein said second female cavity section aligns with the first raised male rim to guide and seat said members together.

11. The nipple implant system of claim 9 wherein the first magnetic member in the nipple prosthetic base is encased in acrylic.

12. The nipple implant system of claim 11 wherein the acrylic ring is formed of biocryl.

* * * * *